United States Patent [19]
Sieber

[11] Patent Number: 4,915,683
[45] Date of Patent: * Apr. 10, 1990

[54] ANTIVIRAL METHOD, AGENTS AND APPARATUS

[75] Inventor: Fritz Sieber, Brookfield, Wis.

[73] Assignee: The Medical College of Wisconsin, Inc., Milwaukee, Wis.

[*] Notice: The portion of the term of this patent subsequent to Oct. 4, 2005 has been disclaimed.

[21] Appl. No.: 24,150

[22] Filed: Mar. 10, 1987

Related U.S. Application Data

[63] Continuation-in-part of Ser. No. 933,697, Nov. 21, 1986, Pat. No. 4,775,625.

[51] Int. Cl.$^4$ .................... A61M 37/00; C12N 7/06
[52] U.S. Cl. ..................... 604/4; 514/274; 435/236; 435/238; 604/5; 604/416
[58] Field of Search ............ 435/238, 236; 424/3, 424/89; 514/274; 544/300, 319; 604/4, 5, 6, 416

[56] References Cited

U.S. PATENT DOCUMENTS

| | | | |
|---|---|---|---|
| 3,110,308 | 11/1963 | Bellamy Jr. | 128/214 |
| 3,140,716 | 7/1964 | Harrison et al. | 128/399 |
| 4,321,919 | 3/1982 | Edelson | 128/214 R |
| 4,398,906 | 8/1983 | Edelson | 604/6 |
| 4,424,201 | 1/1984 | Valinsky et al. | 424/3 |
| 4,428,744 | 1/1984 | Edelson | 604/6 |
| 4,464,166 | 8/1984 | Edelson | 604/6 |
| 4,568,328 | 2/1986 | King | 604/6 |
| 4,573,960 | 3/1986 | Goss | 604/6 |
| 4,573,961 | 3/1986 | King | 604/6 |
| 4,573,962 | 3/1986 | Troutner | 604/6 |
| 4,578,056 | 3/1986 | King et al. | 604/6 |
| 4,596,547 | 6/1986 | Troutner | 604/4 |
| 4,623,328 | 11/1986 | Hartranft | 604/4 |
| 4,727,027 | 2/1988 | Wiesehann | 530/380 X |
| 4,748,120 | 5/1988 | Wiesehahn | 435/173 |
| 4,775,625 | 10/1988 | Sieber | 435/238 |

FOREIGN PATENT DOCUMENTS 0196515 10/1986 European Pat. Off. .

OTHER PUBLICATIONS

Sieber et al., Abstract "Antiviral Activity of Merocyanine 540", dated Feb. 15-19, 1987.
O'Brien J. M., Schober S. L., Burns W. H., Krueger G. J., Montgomery R. R., Sieber F: Inactivation of Enveloped Human Pathogenic Viruses by Merocyanine 540-Mediated Photosensitization and its Potential Use in Blood Product Sterilization. Blood 70:333a, 1987 (abstract).
Sieber F., Krueger G. J., O'Brien J. M., Schober S. L., Sensenbrenner L. L., Sharkis SJ: Inactivation of Friend Erythroleukemia Virus and Friend Virus-Transformed Cells by Merocyanine 540-Mediated Photosensitization. Blood 73:345-350, 1989.
Journal of Cellular Physiology, 116: 118-124 (1983), "Susceptibility to Merocyanine 540-Mediated Photosensitization: A Differentiation Marker on Murine Hematopoietic Progenitor Cells", Richard C. Meagher, Fritz Sieber, and Jerry L. Spivak.
Proc. Natl. Acad. Sci. USA, vol. 81, pp. 7584-7587, Dec. 1984, Medical Sciences, "Selective Killing of Leukemic Cells by Merocyanine 540-Mediated Photosensitiza-
(List continued on next page.)

Primary Examiner—Christine M. Nucker
Attorney, Agent, or Firm—Quarles & Brady

[57] ABSTRACT

A method of treating a body fluid which is to be infused so as to inactivate any enveloped viruses in said fluid comprises mixing the body fluid with an effective amount of a photosensitizing agent which will bind to the viruses and/or virus infected cells and photosensitize them, and then exposing the resulting mixture to visible light to excite and inactivate the viruses. An apparatus for use in the method includes at least one container which contains an effective amount of the photosensitizing agent and which has at least one wall which is permeable to visible light. A number of photosensitizing agents which can be used in the method also are disclosed.

3 Claims, 1 Drawing Sheet

OTHER PUBLICATIONS tion", Fritz Sieber, Jerry L. Spivak, and Alison M. Sutcliffe.

*Molecular Basis of Cancer, Part B: Macromolecular Recognition, Chemotherapy, and Immunology,* pp. 227–234, 1985, Alan R. Liss, Inc., "Merocyanine 540-Mediated Photosensitization of Leukemia and Solid Tumor Cells", Fritz Sieber.

*Cancer Research* 46, pp. 2072–2076, Apr. 1986, "Dye-Mediated Photosensitization of Murine Neuroblastoma Cells", Fritz Sieber and Maya Sieber-Blum.

*Blood,* vol. 68, No. 1 (Jul.) 1986, pp. 32–36, "Dye-Mediated Photolysis of Human Neuroblastoma Cells: Implications for Autologous Bone Marrow Transplantation", Fritz Sieber, Sanjay Rao, Scott D. Rowley, and Maya Sieber-Blum.

*Minimal Residual Disease in Acute Leukemia,* 1986, A. Hagenbeek, B. Lowenberg (editors), Martinus Nijhoff Publishers, "Detection and Selective Destruction of Tumor Cells by the Lipophilic Dye", Merocyanine 540, pp. 282–294, Fritz Sieber.

*Transfusion,* vol. 26, No. 5, 1986, pp. 481–483, "*Inactivation of Human T-Cell Lymphotropic Virus, Type III by Heat, Chemicals, and Irradiation*", Gerald V. Quinnan, Jr., Martha A. Wells, Alec E. Wittek, Michael A. Phelan, Ronald E. Mayner, Stephen Feinstone, Robert H. Purcell and Jay S. Epstein.

ANTIVIRAL METHOD, AGENTS AND APPARATUS

RELATED CASE

The present application is a continuation-in-part of my earlier patent application U.S. Ser. No. 933,697, filed Nov. 21, 1986, now U.S. Pat. No. 4,775,625.

FIELD OF THE INVENTION

The present invention relates to the field of medicine. More particularly, it relates to a method of inactivating viruses in body fluids, especially blood and blood products, and agents and apparatus for use in that method.

BACKGROUND OF THE INVENTION

Blood products such as albumin or clotting factors are prepared from large numbers (up to about 20,000) of pooled blood donations. A sizable portion of the contributors to these large pools of blood are probably carriers of pathogenic viruses (e.g., hepatitis, Epstein-Barr, and cytomegalovirus). For most patients the occasional exposure to a virus-contaminated blood product is probably inconsequential. However, the risk is substantial for immunosuppressed patients and patients who are exposed to these products over prolonged periods of time.

One patient group that is considered at risk for being regularly exposed to human blood products are hemophiliacs. There are approximately 40,000 hemophiliacs in the United States and in western Europe who are regularly treated with preparations of factor VIII, a product of blood.

Three precautions are routinely taken by blood collection centers to identify and eliminate blood donations from carriers of pathogenic viruses: (1) Each unit is tested for the presence of hepatitis B antigen; (2) Each unit is tested for antibodies against HIV; and (3) The prospective donor is asked to voluntarily disclose risk factors. The shortcomings of the voluntary disclosure statement are obvious. They are underscored by the high frequency of acquired immunodeficiency syndrome (AIDS) among hemophiliacs who are regularly treated with factor VIII isolated from pooled human blood.

Screening procedures for most viruses may become available, in the future. However, with some viruses, such as HIV, there is a lag phase in which a recently infected donor will test negative although he is infectious. Viruses also can mutate and thus escape immunologic detection systems. Furthermore, to systematically reject as blood donors all identifiable carriers of pathogenic viruses may not be practical because it could severely restrict the donor pool.

In addition to being able to inactivate viruses in soluble blood products, such as albumin and clotting factors, it would be useful to have a method of inactivating viruses in whole blood and cellular blood products, such as red cells, bone marrow cells.

Heat treatments, extraction of virus with solvents and detergents, and treatment with high doses of gamma radiation can be effective means of inactivating viruses. However, since those procedures are rigorous and nonspecific their applicability is limited.

BRIEF SUMMARY OF THE INVENTION

It is an object of the present invention to disclose a method of inactivating viruses in body fluids.

It is a further object to disclose a novel apparatus for use in the method.

It is a still further object to disclose photosensitizing agents for use in the method.

Other objects will be apparent from the description which follows.

It has now been discovered that enveloped viruses and enveloped virus-infected cells in body fluids, including blood and its products, can be inactivated by contacting the fluids or their products with an effective amount of a photosensitizing agent and exposing the resulting mixture to visible light until the viruses and virus-infected cells have been inactivated. The treated body fluids are presumably then safe for infusion into a patient.

For the treatment of blood or bone marrow, the method of the invention offers the following advantages:

1. It is selective. It inactivates enveloped viruses, tumor cells, some normal hematopoietic progenitor cells and some virus-infected cells. It has, however, no obvious effects on mature blood cells, pluripotent hematopoietic stem cells and plasma/serum components.

2. It may be effective against viruses for which routine screening procedures do not yet exist.

3. It does not restrict the available pool of blood donors.

4. It is relatively non-toxic and excess photosensitizing agent or dye can be easily removed.

5. It uses visible light.

The photosensitizing agents which are to be used in the method of the present invention are agents which preferentially bind to the lipids in viruses or virus-infected cells and which do not or bind only minimally to normal blood components. The agents which are preferred for use in the method are merocyanine dyes which do not bind to the DNA and are probably non-mutagenic and which have been used in the past as fluorescent probes to study the structure and function of biological membranes (Cohen et al. J. Membr. Biol., 19, 1–36 (1974)). The merocyanine dyes, have been shown to undergo transient, voltage-dependent fluorescence enhancements in response to electrical stimulation when they are incorporated into excitable membranes (Davila et al., Nature New Biol., 241, 159–160 (1973)) The generation of electrochemical potentials in human (Sims et al., Biochemistry, 13 3315–3330 (1974)) and Amphiuma red cell membranes (Hoffman and Laris, J. Physiol, 239. 519–552 (1974)), enhances the fluorescence of some of these dyes. These probes have been successfully used in the detection of leukemic cells, Valinsky et al., U.S. Pat. No. 4,424,201, and more recently for the selective killing of leukemic cells in bone marrow by agent-mediated photosensitization (Sieber et al., Proc. Natl. Acad. Sci. U.S.A. Vol 81, pp. 7584–7587 Dec. 1984).

The preferred agents are compounds of the formula

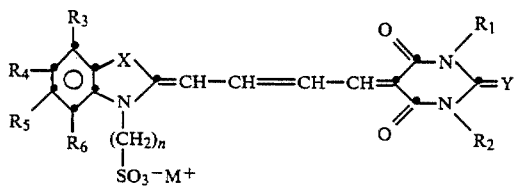

wherein n is 1–5; X is oxygen (O), sulfur (S), —$CR_1$-$R_2$—, or selenium (Se); y is O or S; M is an alkali metal or other basic group; $R_1$ and $R_2$ are the same or different alkyl groups of 1 to 8 carbons; and $R_3$, $R_4$, $R_5$, and $R_6$ are selected from hydrogen, lower alkyl groups of 1 to 5 carbons, lower alkoxy groups of 1 to 5 carbons, phenyl lower alkyls, such as phenylmethyl; or $R_3$ and $R_4$, or $R_4$ and $R_5$, or $R_5$ and $R_6$ are part of an aromatic ring.

The method of the invention may be practiced on a continuous basis using a known apparatus, such as disclosed in Edelson U.S. Pat. No. 4,321,919, which is incorporated by reference herein, or on a batch basis using the novel apparatus of the present invention.

The novel apparatus of the present invention is particularly adapted for the collection, handling, treatment of a sample of a body fluid, especially blood and blood products, with the photosensitizing agent and light and storage of sample until time of use. The preferred apparatus comprises at least one inert, biocompatible, sterile container permeable to visible light which contains an effective amount of the photosensitizing agent to inactivate the viruses in the body fluid to be collected when the container and its contents are exposed to visible light. The container may be connected to other containers to form a closed system. Preferably the container is of a disposable transparent plastic, such as polyvinyl chloride resin, which has been used in the collection and handling of blood. The preferred apparatus also includes a length of collection tubing attached at one end to the container and having at the other end a needle or catheter for collecting blood or another body fluid.

The light source for use with the method of the present invention includes any light source that will provide visible light of a suitable wave length for the desired length of time. Especially preferred is the light source of the photopheresis system available from the THERAKOS Division of Johnson and Johnson Cardiovascular of King of Prussia, Pa. under the trade name UVAR.

The exact mechanism of inactivation of viruses by the method of the present invention is not yet fully understood. The currently available data are compatible with the following model: The photosensitizing agent binds preferentially to disordered or cholesterol-free domains in lipid bilayers of the virus. Binding to proteins, carbohydrates and chromatin is minimal. High affinity binding sites for the agent exist on electrically excitable cells, certain classes of immature blood cells, leukemia cells, some solid tumor cells, and, probably enveloped viruses and some virus-infected cells. Photoexcitation of membrane-bound agent molecules leads to the formation of reactive oxygen species, such as singlet oxygen, which cause lipid peroxidation. Secondary photoproducts may react with plasma membrane and intracellular components.

Based on my present theory, the photosensitization will only be effective with enveloped viruses, but if it turns out that the method is effective on non-enveloped viruses, a different mechanism may be involved.

Variables which can affect the method are agent concentration protein/lipid concentration, protein/lipid composition, geometry and optical properties of the container, intensity and spectral properties of the light source and duration of the illumination. Those skilled in the art will appreciate that each of those variables can be varied within rather wide margins, provided the other variables are adjusted accordingly.

DESCRIPTION OF THE PREFERRED EMBODIMENT

Figure 1:
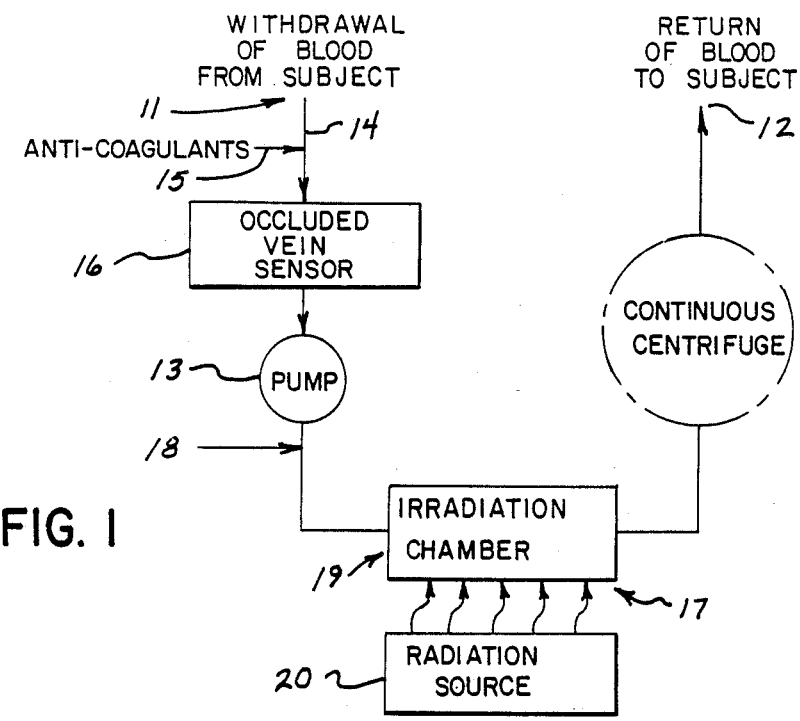
FIG. 1 is a schematic flow diagram illustrating a preferred embodiment of a system operating in accordance with the present invention.

In FIG. 1 herein a schematic diagram is shown of a system 10 for use with the method of the present invention. It is the system of U.S. Pat. No. 4,321,919, supra.

As shown schematically in FIG. 1, blood may initially be withdrawn from the human subject, as at 11. Typically the blood is withdrawn via a donor needle, which may be placed in the right antecubital vein. In the system 10 of FIG. 1, it is assumed that the processing of blood is conducted on a continuous basis from 11 to a final return of the blood to the subject at 12. The return at 12 is via a recipient needle positioned in the left antecubital vein. Where the method is continuous a typical blood flow is in range of from about 10 to 75 ml/min. with a preferred range being from about 40 to 50 ml/min. The desired flow rates are produced by a pump 13, which is positioned in the extracorporeal blood flow stream generally indicated as 14.

Anti-coagulants are preferably injected into the extracorporeal blood flow stream at 15, close to the point of blood withdrawal. Such anti-coagulants can comprise solutions of acid, citrate and dextrose and/or heparin, or of other known anti-coagulant compositions. An occluded vein sensor 16 is preferably provided in stream 14 to prevent or inhibit the generation or continued existence of bubbles in the blood flow stream.

In the preferred mode of practicing the continuous mode of the method of the present invention, the photosensitizing agent is added to the blood after it leaves the human. Thus, as shown in the system 10 of FIG. 1, the agent may be added to the flowing blood downstream of pump 13, and just upstream of where the blood enters the irradiation station 17.

The photosensitizing agent is usually first dissolved in an isotonic solution, which thereafter is directly injected into the flowing blood stream, as at 18. The agent is injected at a rate which takes into account the blood flow rate and achieves a concentration of the agent in the blood in the desired range as the blood passes through the irradiation station 17.

It will be appreciated that the photosensitizing agent may not need to be directly introduced by injection into the extracorporeal blood stream 14. It also might be possible to obtain the desired concentration of the agent by orally or otherwise administering the compound directly to the patient. Alternate modes of administration of the photosensitizing agents are within the scope of this invention and the doses appropriate therefor will be apparent to those skilled in the art.

The introduction of the photosensitizing agents to the extracorporeal stream is preferred because it makes it possible to achieve more exact concentration levels; and to avoid or minimize possible side effects and the like, which can occur from administration of any drug directly to the body system.

At irradiation station 17, which consists of an irradiation chamber 19 and radiation source 20, the blood containing the desired concentration of dissolved photosensitizing agent, is subjected to visible light and preferably visible light having the bulk of its spectral components in the preferred orange to green range for the activation of the particular photosensitive agent being employed in the treatment being conducted. The irradiation station 19 is constructed so as not to block radiation in the desired portion of the visible light spectrum and to present the body fluid from being overheated and damaged.

Figure 2:
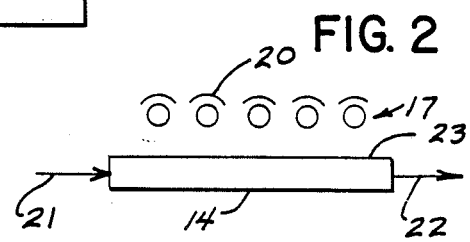
FIG. 2 is a schematic elevational view of the irradiation station portion of the FIG. 1 system.

In FIG. 2, a schematic view appears of an irradiation station 17 of a type suitable for use with the invention. The preferred station 17 consists of a blood treatment or irradiation chamber 19, having an inlet 21 and an outlet 22, enabling blood flow through the chamber, and a spaced source 20 of visible light. The chamber 19 can take various forms, with the principal requirement that it have at least one wall 23 which is substantially transparent to visible light. The chamber (or at least wall 23) therefore can be comprised of various substantially visible light transparent plastics, such as polyvinyl chloride and the like.

In the irradiation chamber 19, the body fluid to be treated flows through a flow passage which is of relatively thin cross-section e.g., about 2 mm thick. The total surface area of the flow passage in the chamber 19 is calculated to provide the blood contained therein with the desired radiation dose level from the visible light source 20. Especially preferred is an apparatus consisting of a plurality of fluorescent tubes with concentric jackets spaced from the tubes to form the flow passages for the body fluid to be irradiated.

The visible light source can comprise commercially available lamps, numerous types of which are known in the art. By way of example, source 20 can comprise a single incandescent or fluorescent lamp or multiple lamps which preferably emit visible light in the orange to green spectrum, i.e., between about 5000 to about 6500 Angstroms, which is preferred when a merocyanine dye is the photosensitizing agent being employed in the method of the invention. With the continuous flow rates utilized in accordance with one aspect of the invention, such a source will provide the desired amount of absorbed energy in the flowing blood for practicing the method of the invention.

The blood flow from irradiation station 17 proceeds as shown in FIG. 1 via outlet 22 back to the subject at 12. Optionally, however, prior to returning the treated blood to the patient, it may be heat exchanged so as to adjust its temperature to that of the patient's circulating blood. Heat exchange may be necessary whenever the treated blood, by consequences of its treatment, has attained a temperature substantially at variance with that of the patient.

Regardless of which photosensitizing agent is employed in the invention or at what rate it is administered the burden placed upon the body's organ system can be further alleviated, by utilizing in conjunction with the present system, a continuous centrifuge (or other filtration system), which device can be used to separate photosensitizing agents.

Figure 3:
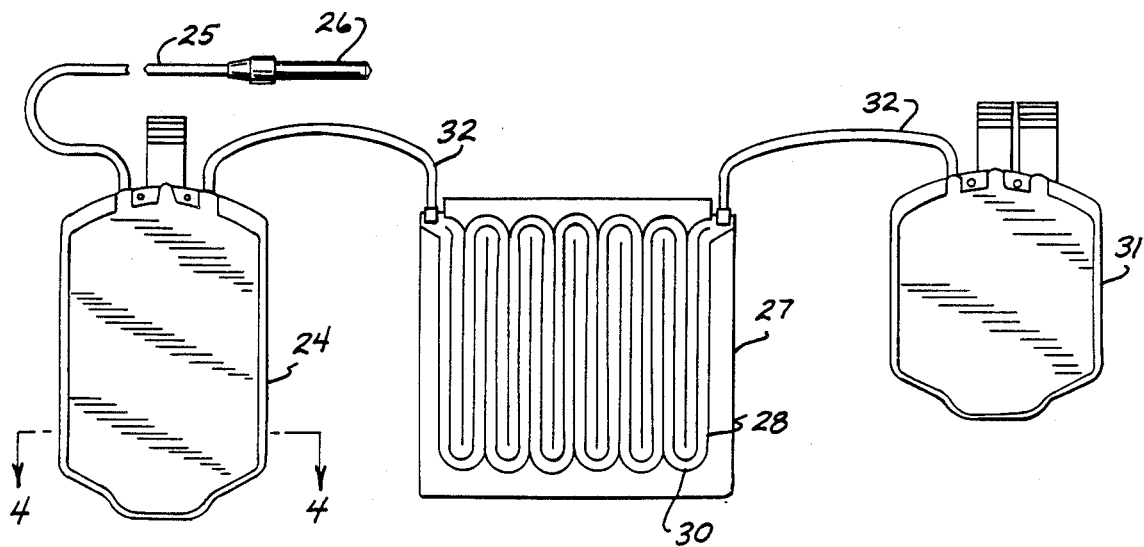
FIG. 3 is a perspective view of a preferred embodiment of an apparatus of the present invention.
Figure 4:
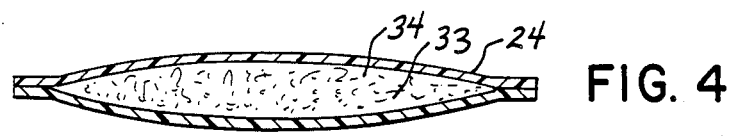
FIG. 4 is a cross sectional view taken along lines 4—4 of FIG. 3.

The preferred embodiment of the apparatus of the invention which is used when whole blood is collected, treated to inactivate viruses and stored to be later administered to the donor or another human is shown in FIGS. 3 and 4. The apparatus as seen in FIG. 3 comprises a first container 24, which is provided with collection tubing 25 and a needle 26; an irradiation chamber 27 comprising a flat, plastic envelope 28 with a continuous flow passage 30; a storage container 31; and tubing 32 which connects the first container 24, the irradiation chamber 27 and the storage container 31 into a closed system. The body fluid can be transferred from the container 24 to the irradiation chamber 27 where it is exposed to visible light and maintained at a safe temperature e.g., by a water bath. It is then transferred to the storage container 31. The body fluid can be transferred through the system by squeezing the first container 24 and/or by use of a tubing pump (not shown). Alternatively, the novel apparatus may take the form of a single container, containing the photosensitizing agent, in which the body fluid can be collected, treated with visible light and stored.

In the apparatus of FIG. 3, an effective amount of anticoagulant liquid 33 containing the photosensitizing agent represented by dots 34 is already in the first container 24. Of course, the agent 34 may be added to the apparatus at any time prior to treatment of the blood or blood products with the visible light. The apparatus and its contents are preferably agitated to bring the agent into contact with the viruses in the body fluids before treating the mixture with visible light to inactivate the viruses. If the body fluid is blood it can then be divided into its various components either before or after addition of the photosensitizing agent and/or exposure to visible light. Any excess photosensitizing agent can, if desired, be removed any time after the light exposure by conventional means.

In those embodiments of the inventions in which the product containing the viruses to be inactivated is not blood collected directly from a donor, the photosensitizing agent may be added to the product immediately prior to light exposure. For example, when the product is a cell-free blood product, it is first dissolved or suspended in an aqueous medium; when the product is blood cells they are first suspended in a physiological medium and when the product is bone marrow or blood cells, it is preferred to suspend it in deuterium oxide ($D_2O$) because the presence of $D_2O$ shortens the illumination time required, presumably by extending the half life of singlet oxygen. The photosensitizing agent is then added to the solution or suspension and the resulting mixture stirred or otherwise agitated to bring the agent into contact with the viruses or virus infected cells. The mixture is then exposed to visible light of a suitable wavelength. In an aqueous environment the preferred excitation spectrum peaks are at 510 and 535 nm and in an organic phase, the spectrum is redshifted to 565 nm. After completion of the photosensitization step the excess agent may be separated by centrifugation. If desired, undesired components such as plasma proteins, can be separated from the mixture by precipitation with solvents or salt, solvent extractions, or by chromatographic means.

Representative of the specific agents that can be used are the following:

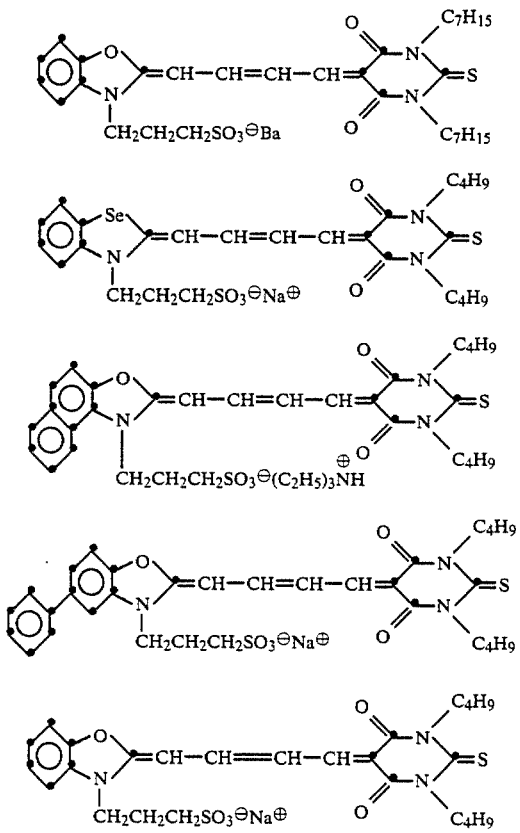

The photosensitizing agent is employed in an amount which is effective under the conditions of use to accomplish the inactivation of the viruses which may be present. Some of the agents, of course, are more active than others and can be used in smaller amounts. The toxicity of the preferred merocyanine dyes is very low. Therefore, it is not essential that they be completely removed from the treated body fluid, blood, blood product or bone marrow before administration to a patient.

The merocyanine, MC 540, is normally used with light of suitable wavelength n an amount of about 10 micrograms to about 25 micrograms per milliliter of body fluid and a more active merocyanine derivative, MC 540A, is used in an amount of about 5 micrograms to about 10 micrograms per milliliter under comparable conditions.

The effective wavelengths of visible light that can be used vary greatly; however, it is generally desired that the light be of a wavelength in the green to orange range when the agent is a merocyanine dye. It appears that blue light and dark red light is not particularly effective with the preferred merocyanine dyes.

Tests have shown that:

(1) Suspensions of Friend virus, Friend virus-transformed cells, Herpes simplex, cytomegalovirus, HTLV-I and HTLV-I infected cells are rapidly inactivated by MC 540-mediated photosensitization.

(2) The same treatment protocol does not affect mature blood cells and normal pluripotent hematopoietic stem cells in mouse and man.

(3) Photosensitized plasma clots normally, suggesting that at least some clotting factors are still intact.

(4) The small amounts of dye that are transferred with photosensitized bone marrow cells are not toxic to mice (i.e., about 100,000 times less than the $LD_{10}$ of the compound in mice).

The simultaneous exposure to MC 540 or MC 540A and visible light kills human and murine leukemia, lymphoma, and neuroblastoma cells very rapidly, but normal pluripotent hematopoietic stem cells and mature blood cells very slowly. This differential sensitivity to MC 540-mediated photolysis can be used to purge simulated autologous remission marrow grafts (mixtures of normal marrow cells and tumor cells) of residual tumor cells.

These findings have obvious implications for the treatment of patients with leukemia or disseminated solid tumors. Such patients could benefit from a treatment regimen that combines very intensive (i.e., marrow-ablative) chemo- and/or radiotherapy with a bone marrow transplant. (The very intensive chemo- or radiotherapy has a better chance of eradicating the tumor. The bone marrow transplant rescues the patient from this otherwise lethal therapy.) However, most patients are currently ineligible for this therapeutic modality because they lack compatible marrow donors or because their age predisposes them to develop severe forms of graft-versus-host disease even if the marrow graft originated from an HLA-identical allogeneic donor. Autotransplantation of the patient's own cryopreserved remission marrow obviates the need for matched donors and virtually eliminates graft-versus-host reactions. However, autotransplantation of remission marrow carries a significant risk of reinfusing occult tumor cells unless the tumor cells are removed or killed by a suitable extracorporeal purging procedure.

Based on knowledge acquired about the molecular mechanisms that control a cell's affinity for MC 540, we hypothesized that MC 540 should also react with enveloped (i.e., lipid-containing) viruses. We tested this hypothesis with a transplantable mouse leukemia virus (the Friend erythroleukemia virus complex), the human T cell leukemia virus, HTLV-I, Herpes simplex 1 and cytomegalovirus. Friend virus was obtained from cell-free supernatants of cultured erythroleukemia cells or as a cell-free extract of spleen or bone marrow cells from infected animals. Simultaneous exposure to MC 540 (15 ug/ml) and light (40 $J/cm^2$) reduced the virus titer by $\geq 4$ logs regardless of the origin of the virus preparation. Animals that were injected with photosensitized virus preparations developed neither splenomegaly nor polycythemia, nor leukemia. Virus-infected spleen cells, bone marrow cells, and cultured Friend erythroleukemia cells were inactivated at about the same rate as cell-free virus preparations. By contrast, bone marrow grafts that were subjected to the same treatment with MC 540 and light were still capable of rescuing lethally irradiated recipients.

HTLV-I was also susceptible to MC 540-mediated photosensitization. The amount of virus that could be sedimented by centrifugation was reduced 5-fold after treatment with MC 540 and light. The remaining 80% of the virus were probably lysed. The small fraction that was sedimented was visibly stained by MC 540. It is conceivable that the sedimented virus fraction, although not lysed, had sustained enough photodynamic damages to make it noninfectious. For example, when the virus is Herpes simplex 1 the order of magnitude reduction may be as high as 90.

An analog of MC 540 which we have labeled MC 540B (see structural formula below) reduces illumination times about 6-fold when used in equimolar concentrations.

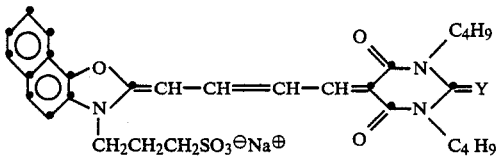

Merocyanine-mediated photolysis of tumor cells and viruses appears to be primarily mediated by singlet oxygen. An additional 2-fold reduction in illumination time can therefore be achieved by performing the photosensitization step in the presence of deuterium oxide ($D_2O$).

Unlike heat or high doses of ionizing irradiation, MC 540-mediated photolysis is more selective in its toxicity. Most mature leukocytes and primitive hematopoietic progenitor cells are highly resistant to MC 540-mediated photolysis and the ability of plasma to clot is not impaired. Dye mediated photosensitization may be the preferred antiviral treatment in situations where critical components are temperature or radiation sensitive. The acute systemic toxicity of MC 540 is low. The amount of dye that is injected with a typical mouse bone marrow graft is more than 100,000 times less than the $LD_{10}$ in the same species.

The invention is further illustrated by the following examples.

EXAMPLE 1

When cultured F4-6 erythroleukemia cells, spleen or marrow cells from diseased animals, cell-free extracts of cultured cells, spleen cells, or marrow cells, or cell-free supernatants of F-6 cultures were injected into healthy B6D2F1 mice, the spleen weights increased from 70 mg to about 2 g within two weeks. The animals became polycythemic and, eventually, died. When cell suspensions, cell-free extracts, or culture supernatants were photosensitized and exposed to light prior to injection, spleen weights remained normal, hematocrits remained normal, and the animals survived. Normal pluripotent hematopoietic stem cells (as determined by the ability of photosensitized marrow cells to rescue lethally irradiated syngeneic hosts) were spared by the photosensitization treatment. Virus preparations that were exposed to dye or light alone caused splenomegaly, polycythemia, and death. A series of experiments thus showed that MC 540-mediated photolysis inactivates cell-free Friend virus, intracellular Friend virus, and Friend virus-infected cells.

EXAMPLE 2

Experiments with human herpes simplex virus type 1 (HSV-1), and human T-cell leukemia virus type I (HTLV-I) produced similar results. Herpes simplex-1 was extremely susceptible to MC 540 mediated photolysis. A limiting dilution plaque forming assay on Vero cells indicated a $\geq 5$ log reduction (limit of detection) of the virus titer after only 5 min. of illumination. The standard illumination protocol calls for 90 min. of illumination. It is thus conceivable that we can reduce the titer by 90 log. With human cytomegalovirus we observed a more than 7 log reduction in 15 minutes. Infectivity assays for HTLV-I have, unfortunately, not yet been developed. We therefore used reverse transcriptase activity as an indicator of virus destruction. Photosensitized and untreated aliquots of the same virus suspension were pelleted on a sucrose cushion. The pellet of the treated aliquot was about 5 times smaller and visibly red. Its reverse transcriptase content was reduced by more than 80% (Table 1). The balance of the enzyme activity was recovered in the supernatant. More than 80% of the original virus mass was apparently damaged so extensively (virtually "dissolved") that it was no longer pelletable by a two hour spin at 100,000 $\times$g. If the photosensitization of enveloped viruses bears any resemblance to the photosensitization of cells, it is reasonable to speculate that the pelletable material was also photodamaged and perhaps no longer infective.

TABLE 1

| HTLV-I, Reverse Transcriptase activity | |
| --- | --- |
| (1) No dye, no light | 194,268 cpm |
| (2) MC 540, no light | 208,548 cpm |
| (3) No dye, light 90 min | 158,016 cpm |
| (4) MC 540, light 90 min | 37,848 cpm |

EXAMPLE 3

The acute systemic toxicity of MC 540 was determined by injecting groups of 10 BAF1 mice intravenously with graded scale and fitted with a least square regression line to determine $LD_{10}$ and $LD_{50}$ (Table 2). It should be pointed out that MC 540 is not more toxic than the fluorescent dyes that are commonly used for the angiography of the retina. Necropsies showed that the probable cause of death after high doses of MC 540 was the formation of large emboli of precipitated dye in major blood vessel (i.e., we killed the mice by exceeding the solubility of the dye in plasma).

TABLE 2

| Acute Toxicity of MC 540 | |
| --- | --- |
| $LD_{10}$ (mouse) | 55 mg/kg |
| $LD_{50}$ (mouse) | 84 mg/kg |
| Injected with photosensitized marrow graft | 0.0004 mg/kg |
| For comparison | |
| $LD_{50}$ (mouse) fluorescein | 300 mg/kg |
| $LD_{50}$ (mouse) indocyanine green | 70 mg/kg |

EXAMPLE 4

Red blood cells (concentration $1.2 \times 10^9$/ml) containing Herpes simplex-1 and 15 ug/ml of MC 540 and 25 ug/ml of MC 540, respectively, were exposed to visible light from an illumination cell (15 mm). After 15 minutes of MC 540 mediated photosensitization no live virus was detected in the mixture containing 25 mg/ml of MC 540. Similar results were noted after 70 minutes in the mixture containing 15 ug/ml of the MC 540.

It will be readily understood by those skilled in the art that the foregoing description has been for purposes of illustration only and that a number of changes may be made without departing from the scope of the invention. For example, the containers of the novel apparatus may take a wide variety of shapes and forms. In addition to being shaped like conventional blood bags, they can also be elongated tubes or other shapes. Further, the agent need not be physically in the containers as long as it can be added thereto before or after the addition of the body fluid, preferably without opening the system to the outside. Therefore, it is intended that the invention not be limited except by the claims.

I claim:

1. The method of treating a body fluid to inactivate viruses therein which comprises first bringing said body fluid into contact with an effective amount of a photosensitizing agent which selectively binds to enveloped viruses and enveloped virus infected cells and then exposing the combination of body fluid and agent to visible light to photosensitize and inactivate the enveloped viruses in said body fluid said photosensitizing agent having the following formula:

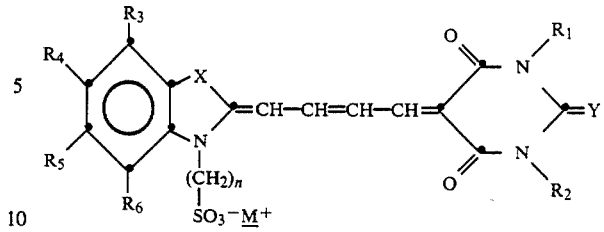

in which n is 1-5, x is oxygen (O), sulfur (S), —$CR_1R_2$— or selenium (Se); y is O or S, M is alkali metal or other basic group; $R_1$ and $R_2$ are the same or different alkyl groups of 1 to 8 carbon; and, $R_3$, $R_4$, $R_5$ and $R_6$ are selected from hydrogen, lower alkyl group of 1 to 5 carbons, lower alkoxy groups of 1 to 5 carbon atoms, phenyl lower alkyls; or $R_3$ and $R_4$, or $R_4$ and $R_5$, or $R_5$ and $R_6$ are part of an aromatic ring.

2. The method of the claim 1 in which the photosensitizing agent is merocyanine 540.

3. In a blood collection system which comprises a sterile, closed blood bag which is transparent to visible light and which has integral blood collection means, the improvement which comprises the interior of said sterile, closed bag prior to the collection of blood containing a safe and effective amount of a merocyanine dye which selectively will bind to any enveloped virus in the blood to be collected so that when the blood is collected and the bag containing the blood and dye is exposed to visible light of sufficient strength for a sufficient length of time any enveloped virus present will be photosensitized and inactivated.

* * * * *

UNITED STATES PATENT AND TRADEMARK OFFICE
CERTIFICATE OF CORRECTION

PATENT NO. : 4,915,683
DATED : April 10, 1990
INVENTOR(S) : Sieber

It is certified that error appears in the above-identified patent and that said Letters Patent is hereby corrected as shown below:

| | |
|---|---|
| Column 7, line 49 | "n" should read --in-- |
| Column 7, line 64 | "HTLV-I" should read --HTLV III-- |
| Column 8, line 49 | "ug/ml" should read --µg/ml-- |
| Column 10, line 62 | "ug/ml" should read --µg/ml-- |
| Column 10, line 63 | "ug/ml" should read --µg/ml-- |
| Column 10, line 66 | "mg/ml" should read --µg/ml-- |
| Column 10, line 68 | "ug/ml" should read --µg/ml-- |

Signed and Sealed this

Seventeenth Day of September, 1991

Attest:

HARRY F. MANBECK, JR.

*Attesting Officer*    *Commissioner of Patents and Trademarks*